United States Patent
Hellmundt et al.

(10) Patent No.: US 10,792,387 B2
(45) Date of Patent: Oct. 6, 2020

(54) DISINFECTANT DISPENSER FOR STORING AND DELIVERING AN AGENT FOR DISINFECTING SURFACES AND/OR SKIN, DISINFECTANT AND METHOD FOR PUBLICALLY SIGNALLING A DISINFECTED STATE OF PERSONS

(71) Applicants: Robert Hellmundt, Apolda (DE); Alexander Döpel, Weimar (DE)

(72) Inventors: Robert Hellmundt, Apolda (DE); Alexander Döpel, Weimar (DE)

(73) Assignee: Heyfair GmbH, Jena (DE)

( * ) Notice: Subject to any disclaimer, the term of this patent is extended or adjusted under 35 U.S.C. 154(b) by 44 days.

(21) Appl. No.: 15/760,427

(22) PCT Filed: Sep. 14, 2016

(86) PCT No.: PCT/EP2016/071708
§ 371 (c)(1),
(2) Date: Mar. 15, 2018

(87) PCT Pub. No.: WO2017/050619
PCT Pub. Date: Mar. 30, 2017

(65) Prior Publication Data
US 2018/0272020 A1  Sep. 27, 2018

(30) Foreign Application Priority Data

Sep. 21, 2015 (DE) .......................... 10 2015 218 040

(51) Int. Cl.
*A61L 2/28* (2006.01)
*A61L 2/18* (2006.01)
(Continued)

(52) U.S. Cl.
CPC .................. *A61L 2/28* (2013.01); *A61L 2/18* (2013.01); *G08B 21/245* (2013.01); *G16H 40/20* (2018.01)

(58) Field of Classification Search
CPC .. A61L 2/28; A61L 2/18; G16H 40/20; G08B 21/245
See application file for complete search history.

(56) References Cited

U.S. PATENT DOCUMENTS

| 5,152,431 A | 10/1992 | Gardner et al. ............... 222/136 |
| 6,139,821 A | 10/2000 | Fuerst et al. .................... 424/59 |

(Continued)

FOREIGN PATENT DOCUMENTS

| CN | 201537558 U | 8/2010 | ............... A61L 2/18 |
| EP | 1163913 A2 | 12/2001 | ............... A61L 2/28 |

(Continued)

OTHER PUBLICATIONS

Linguee translation, Evidence, NPL (Year: 0).*

(Continued)

*Primary Examiner* — Sean E Conley
*Assistant Examiner* — Brendan A Hensel
(74) *Attorney, Agent, or Firm* — Bodner & O'Rourke, LLP; Gerald T. Bodner; Christian P. Bodner

(57) ABSTRACT

The invention relates to a disinfectant dispenser configured to store and dispense a surface and/or skin disinfectant, the disinfectant dispenser including a first storage container including a disinfectant; a second storage container (4) a including marking agent, wherein the marking agent is inactive in the second storage container; and a mixing section in which the marking agent is mixed with the disinfectant when the disinfectant dispenser is actuated, wherein the marking agent is provided in an inactive state (Continued)

after it is dispensed from the disinfectant dispenser. The disinfectant includes a disinfecting base component and a marking agent that is mixable with the base component, wherein the marking agent is inactive before it is mixed with the disinfecting base component and after mixing and applying the disinfectant to a surface the marking agent marks the disinfected surface through a coloration in a manner that is detectable by the human eye and also technically detectable, wherein the marking effect subsides with a subsiding disinfection state. The method for public signaling of a disinfection state of persons includes the steps: applying a disinfecting mix including a disinfecting component and a marking component to a skin area to be disinfected at a disinfection station and/or from a portable disinfectant dispenser; coloring the skin area to be disinfected by the marking component during the disinfection process; visible persistence of the coloration on the disinfected skin area, wherein the disinfected state of the skin area is signaled in a generally perceivable and detectable manner; and subsiding of the persistence of the coloration at the latest with subsiding sterility of the skin area, wherein a discoloration or change in color caused thereby is also signaled in a generally perceivable and detectable manner.

9 Claims, 4 Drawing Sheets

(51) Int. Cl.
   *G08B 21/24*       (2006.01)
   *G16H 40/20*       (2018.01)

(56) References Cited

U.S. PATENT DOCUMENTS

| | | | |
|---|---|---|---|
| 7,053,029 B2* | 5/2006 | MacDonald | A61K 8/368 |
| | | | 510/130 |
| 2005/0090414 A1 | 4/2005 | Rich | 510/136 |
| 2009/0093063 A1* | 4/2009 | Anslyn | A61K 8/11 |
| | | | 436/164 |
| 2014/0158641 A1* | 6/2014 | Mukherjee | C02F 1/32 |
| | | | 210/764 |
| 2014/0327545 A1* | 11/2014 | Bolling | G08B 21/245 |
| | | | 340/573.1 |
| 2015/0216985 A1 | 8/2015 | Macoviak et al. | 424/10.3 |
| 2016/0310231 A1* | 10/2016 | Cohen | A61B 90/80 |

FOREIGN PATENT DOCUMENTS

| | | | | |
|---|---|---|---|---|
| EP | 1184071 A1 | 3/2002 | | B01F 15/02 |
| WO | WO9008558 A1 | 8/1990 | | A01N 59/00 |
| WO | WO9505998 A1 | 3/1995 | | B05B 11/00 |
| WO | WO0022260 A1 | 4/2000 | | A47K 1/00 |
| WO | WO2007090387 A2 | 8/2007 | | A61B 19/00 |
| WO | WO2008060355 A2 | 5/2008 | | A01N 25/00 |
| WO | WO2008112073 A2 | 9/2008 | | B67D 7/58 |
| WO | WO2012042243 A1 | 4/2012 | | A01N 25/04 |
| WO | WO2013030597 A2 | 3/2013 | | A61L 2/18 |

OTHER PUBLICATIONS

The Notification Concerning Transmittal of International Preliminary Report on Patentability (Chapter I of the Patent Cooperation Treaty), in English, dated Apr. 5, 2018, which was issued by the International Bureau of WIPO in Applicants' corresponding international PCT application having Serial No. PCT/EP2016/071708, filed on Sep. 14, 2016.

The English translation of the International Preliminary Report on Patentability (Chapter I of the Patent Cooperation Treaty), dated Mar. 27, 2018, which was issued by the International Bureau of WIPO in Applicants' corresponding international PCT application having Serial No. PCT/EP2016/071708, filed on Sep. 14, 2016.

The Written Opinion of the International Searching Authority, in English, dated Apr. 12, 2017, which was issued by the International Bureau of WIPO in Applicants' corresponding international PCT application having Serial No. PCT/EP2016/071708, filed on Sep. 14, 2016.

The International Search Report, in English, dated Apr. 12, 2017, which was issued by the International Bureau of WIPO in Applicants' corresponding international PCT application having Serial No. PCT/EP2016/071708, filed on Sep. 14, 2016.

* cited by examiner

DISINFECTANT DISPENSER FOR STORING AND DELIVERING AN AGENT FOR DISINFECTING SURFACES AND/OR SKIN, DISINFECTANT AND METHOD FOR PUBLICALLY SIGNALLING A DISINFECTED STATE OF PERSONS

The invention relates to a disinfectant dispenser for storing and delivering an agent for disinfecting surfaces and/or skin according to claim 1, a disinfectant according to claim 7 and method for public signaling a disinfected state of persons according to claim 16.

Disinfectants and methods for using disinfectants are known in the art. Thus e.g. U.S. Pat. No. 7,053,029 B2 uses a soap whose application is being signaled. The soap includes an indicator agent which goes through a color transition or a viscosity change after a predetermined time period which signals to the user that a cleaning process performed by the soap, for example washing hands has to be performed with a particular time minimum. A change of the indicator signals to the user that the required time minimum of the washing process has been reached.

U.S. Pat. No. 6,139,821 discloses materials and methods using a temporary visual indicator. The printed document teaches a sunscreen agent with an indicator that is visible when applied to the skin but which transitions into an invisible state briefly after application. The indicator however remains on the skin and can be reactivated as required so that it can be checked whether the sunscreen is still present on the skin with a sufficient amount. The indicator is not visible during normal applications so that a disadvantageous interference with the sunscreen effect is prevented and tanning of the skin is not impaired by shading.

Furthermore soaps and disinfectants are known from various printed documents e.g. the WO 2008 112073 or WO 2008/060355 A2 wherein impact times are indicated on the hand or on surfaces and instruments that are to be disinfected, wherein it shall be signaled for example whether the applied disinfectant is not in a combust able state any more.

Thus, the recited disinfectants indicate correct use and signal to persons who directly use the disinfectants for example a surgeon, a treating doctor or hospital personnel that is responsible for disinfecting medical equipment that the portion to be disinfected is in a correct state.

In areas with high public traffic, in particular hospitals, hospitals wards but also in public buildings, government offices and in other places where for example increased cleanliness is required or where a risk of transmittable diseases due to a high density of people is particularly high and therefore the places have to be secured by corresponding cleanliness and disinfecting measures, the recited disinfectants however cannot be used. The fact that a disinfectant has been used correctly, thus for example the disinfection process has taken long enough and can be terminated now is only indicated to the direct user.

However contrary thereto it is important that anybody within the public in the medical area, the public building or the government office can obtain a reasonable level of certainty that surrounding persons have undergone disinfection procedures. In this case it is only of secondary importance whether somebody has washed their hands long enough or rubbed them with disinfectant. It is much more important to known whether someone has disinfected themselves at all in order to determine precisely and quickly whether a person is allowed in a particular area or not. The known disinfectants are not useable for this purpose.

Thus, it is an object of the invention to provide devices and methods that allow a signaling of a disinfection state of any individual person without complication wherein the signaling is public and visible for everybody without any ambiguity. If particular devices are required for this purpose they shall be easy to handle, function safely and shall be installable with minimum complexity.

This disinfection state of the person shall be trace able for a sufficiently long time period also when the disinfection process as such has already occurred some time ago. The issue is here in particular a reliable signaling regarding when the disinfected state is not provided anymore or has not been provided from the beginning.

It is another object to provide a communication method which facilitates public signaling of the disinfection state in an overall simple manner.

The objects are achieved by a disinfectant dispenser with the features of claim 1, a disinfectant with the features of claim 6 and a method for public signaling of a disinfection state with the features of claim 13. The dependent claims include useful or advantageous embodiments of the disinfectant dispenser, the disinfectant or the signaling method.

The disinfectant dispenser for storing and dispensing a surface disinfectant agent comprises a first storage container with a disinfectant agent included therein. A second storage container with a marking agent included therein wherein the marking agent is inactive within the second storage container and a mixing section in which the marking agent is mixed with the disinfectant agent when the disinfectant agent dispenser is actuated.

The marking agent is provided in an unstable state after being retrieved from the disinfectant agent dispenser.

The basic idea of the claimed disinfectant dispenser is marking a disinfectant with this device. The marking agent is mixed by the disinfectant agent dispenser with the disinfectant agent. The marking agent is disposed on the disinfected area after the disinfecting method together with the disinfectant agent, for example on the disinfected hand. The marking agent is inactive within the disinfectant dispenser and can be stored for any time period. After mixing it with the disinfectant agent at the latest after dispensing the marking agent and after applying it on the disinfected surface the marking agent is activated and decomposes over time while remaining visible for a sufficient time period. It is the core idea of the invention is to configure the disinfectant dispenser simultaneously as a device that is useable to mark persons thus so that the disinfection can be functionally combined with marking the persons so that the marking disappears again after a certain time period.

In another embodiment the disinfectant dispenser includes an activation section in which the marking agent is transferable from an inactive state into the activated state. This section is used for influencing the marking agent included in the disinfectant dispenser so that the marking agent can perform its marking function but does not decompose in the supply of the disinfectant dispenser.

The activation section can be configured in various ways.

In a first embodiment the activation section includes a heat input device wherein the heat input is configured to transform the marking agent into the activated state.

In the second embodiment the activation section includes a device for introducing electromagnetic radiation wherein the electromagnetic radiation is configured to cause the transformation of the marking agent into the activated state. This can be for example ultraviolet radiation which cracks the molecule formation of the marking agent, wherein the reaction products are on the one hand side unstable and on the other hand side generate a corresponding coloration and are therefore configured for marking.

In a third embodiment the activation section is a reologically effective device configured to influence the flow properties and/or an internal friction of liquids wherein the reologic device is configured to cause a release of microencapsulated marking material volumes into the volume of the disinfectant. Thus it is possible to use an inner friction of a flowing liquid so that the marking agent is released from a stabilizing encapsulated form and thus activated while the marking agent can simultaneously fulfill the time limited marking function.

In one embodiment the disinfectant dispenser is configured as a double wall container, in particular as a double wall collapsible tube, wherein the storage container for the marking agent is formed by the inner cavity or the double wall cavity of the container. An embodiment of this type is suitable in particular for portable disinfectant dispensers.

A disinfectant for surface disinfection of objects and body parts according to the invention includes a disinfecting base component and a marking agent that is optionally mixable into the base component. Before mixing the marking agent into the base component that is to be disinfected the marking agent is stable and marks a surface after the marking agent has been mixed in and the disinfectant has been applied to the surface, wherein the marking effect dissipates when the disinfection state subsides.

The disinfectant disinfects and marks at the same time. The disinfecting base component causes the disinfection as such, the marking agent is thus also applied and indicates the disinfection of the respective body part or object. The marking effect of the marking agent dissipates when the disinfecting effect of the disinfecting base component dissipates.

In a first embodiment the marking agent is a visually evident colorant. The marking agent can be a colorant that is florescent in a second embodiment due to energy introduction. In a third embodiment the marking agent can be a colorant that is detectable in the non-visual range. Another possible embodiment in addition to an exclusively visually evident marking is a marking which becomes visible in the non-visual range, for example due to suitable camera systems or through particular excitements, e.g. by radiation with so called black light. This has the advantage that more objective and documentable detection and controlling of persons can be performed which are not possible through more simple viewing with a naked eye and according to an individual assessment of the viewer.

In one embodiment the marking agent is transferable through an interaction with the disinfecting base component or through an external impact from the stable state into the transient or degrade able state. This is exactly the case when the marking agent is used together with the disinfecting component. In this case the marking agent marks the person that is simultaneously disinfected. The marking agent however is degrade able exactly from this point in time, it disappears quasi with the disinfecting effect of the disinfectant component.

The marking agent can also be transformable through the interaction with the disinfecting base component from the stable state into a second meta stable state. Thus, the meta stable state of the marking agent transforms through an interaction with the surface of the disinfected object and/or a surrounding atmosphere into the volatile or degrade able state. In this case the marking agent is not replaced by the disinfecting base component in the actual sense. However, presence of the disinfecting base component is a precondition for the marking agent being degradable for example by the ambient air or by other effects.

In combination therewith the marking effect of the marking agent can also occur and be activated during the volatile or degradable state of the marking agent. This means that the marking agent only has a real marking effect, this means e.g. a coloration is visible while the marking agent is on the disinfected hand together with the disinfectant. However, when the marking agent in on the hand without the disinfectant component it does not mark and no disinfection can be faked. A person thus unmarked is therefore not perceived or registered to be a disinfected person.

When performing a method for public signaling of a disinfection state of persons the following method steps are being performed.

A disinfecting mix is applied that is made from a disinfecting component and a marking component onto a skin area to be disinfected at a disinfection station and/or from a portable disinfectant dispenser. This causes a coloration of the skin area to be disinfected by the marking component during the disinfection process. This causes a visible persistence of the coloration on the disinfected skin area, wherein the disinfected state of the skin area is signaled in a generally perceive able manner. Eventually the persistence of the coloration subsides at the latest when the sterility of the skin area subsides.

When performing the method the general persistence of the coloration of the disinfected skin area starts at the earliest when the disinfecting component causes the sterility of the skin area. This means in particular that no coloration is initially performed directly with the disinfecting. The discoloration starts only when the disinfecting component actually develops its germicide effect and remains the latest until the sterility of the skin area subsides again.

In one embodiment to the invention the visible persistence of the coloration of the skin area is generated by the germicide effect of the disinfecting component wherein the biologic decomposition products thus created generate a visible color reaction in the marking component, this means that the coloration remains as long as the substances remain that are released due to germs being killed by the disinfection process. However when this release is terminated, thus no germs are being killed anymore and the disinfected area is not sterile anymore the coloration is not maintained any more either and the non sterile state is generally visible again due to the lack of coloration.

In one embodiment the marking effect of the marking agent is caused by a molecular switch structure wherein the molecular switch structure only leads to a color perceivable and/or detectable state of the marking agent through a first electromagnetic radiation and is returnable into a non-color perceivable and/or non-detectable state of the marking agent through a second electromagnetic irradiation.

In one embodiment of the method the disinfected and colored skin area is registered by an access control arrangement wherein the access control arrangement provides and blocks an excess of persons as a result of the registration process.

In another embodiment of the method the disinfected an colored skin area is registered by an image capture and image detection arrangement wherein a disinfection monitoring is performed as a result of a performed image capturing and image detection of numbers of persons in a certain area and/or numbers of persons transitioning through predetermined transition areas.

In another embodiment the visible persistence of the coloration on the skin area is triggered by a start of an evaporation process of the disinfecting component wherein this causes a color reaction in the marking component. In this case it is indicated accordingly when the disinfecting component evaporates. It is well known that the disinfecting effect is caused at this exact point in time and now becomes visible by the coloration.

In one embodiment the degradation of the marking component is triggered by the disappearance of the coloration due to the impact of ambient air and/or due to a bleaching caused by the impact of the ambient air. In another embodiment a degradation of the persistence of the marking component is triggered by an impact of a second disinfectant. In this embodiment the use of several different disinfectants can be checked visually.

The disinfectant dispenser, the disinfectant and the method for public signaling of a disinfection state of persons will be subsequently be described in more detail with reference to exemplary embodiments based on drawing FIGS. 1-3. Identical reference numerals are used for identical or equivalent components, wherein.

Figure 1:
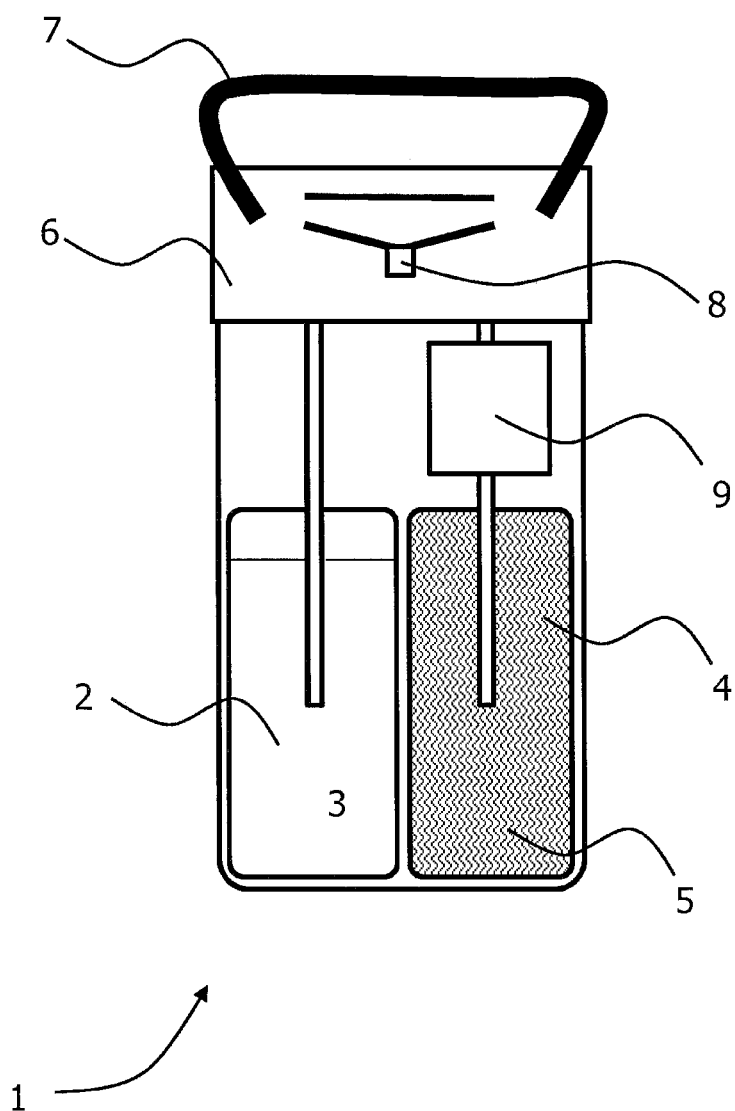
FIG. 1 illustrates a disinfectant dispenser according to the invention for use with a marking disinfectant and for use according to the signaling method according to the invention.

FIG. 1 illustrates an exemplary disinfectant dispenser 1. The disinfectant dispenser 1 includes a first storage container 2. The first storage container includes a disinfectant 3. The disinfectant can be based on different agents. In particular alcohol based as well as non-alcohol based disinfectants can be used.

A second storage container 4 includes a marking agent 5. The disinfectant dispenser illustrated in this embodiment is provided for a stationary application where the device is permanently installed at a particular location, for example in an entry portion to a building. However, a mobile and portable version is also possible that is illustrated in an exemplary manner in FIG. 1a wherein the disinfectant is stored e.g. in a double wall tube in the first tube volume and the marking agent is stored in the second tube volume. By the same token corresponding double wall containers, in particular portable bottles made from plastic material can be provided as disinfectant dispensers. The plastic bottles can for example be distributed to the public in entry areas.

In the embodiment of the disinfectant dispenser illustrated herein a dispensing device 6 is provided which can be actuated in the instant embodiment by a lever 7. Through the actuation the disinfectant 3 and the marking agent 5 are pumped out of their respective storage containers and unite at the latest within an outlet opening 8 to form a marked disinfectant which drips for example onto a hand held thereunder and can be rubbed in at this location so that a skin surface of the hand is disinfected.

Within the storage container 4, e.g. in a corresponding storage container for a mobile or portable version of the disinfectant dispenser the marking agent is in an inactive state. The marking agent can be stored in this container for any amount of time and can be transported. During the pumping process during the dispensing of the disinfectant the marking agent enters an activation section 9 and exits the activation section in an active state. The dispensed marking disinfectant thus represents a mix of the disinfectant and the activated marking agent. Only in this activated state the marking agent develops its marking effect and thus its signal function.

Within the storage container 4 the marking agent is in the inactive state and cannot be used in a marking manner. In this state the marking agent either does not have a marking effect and is for example simply colorless, or it has another color which can be easily differentiated from the actual marking color of the marking agent in the activated state.

The activation section 9 can be configured in different ways and can also be arranged at different position within the disinfectant dispenser. It is possible here in particular that the activation section coincides with the dispensing opening 8 or includes the section in which the disinfectant and the initially inactive marking agent are joined for the first time and thus mixed. In many ways also here the activation of the marking agent can be performed in the activation section.

The activation of the marking agent by the mixing process can be used in particular for a mobile and portable disinfectant dispenser this means for double walls tubes or portable arrangements and small bottles. The double wall devices include an inner cavity A and a double wall cavity B.

Figure 1A:
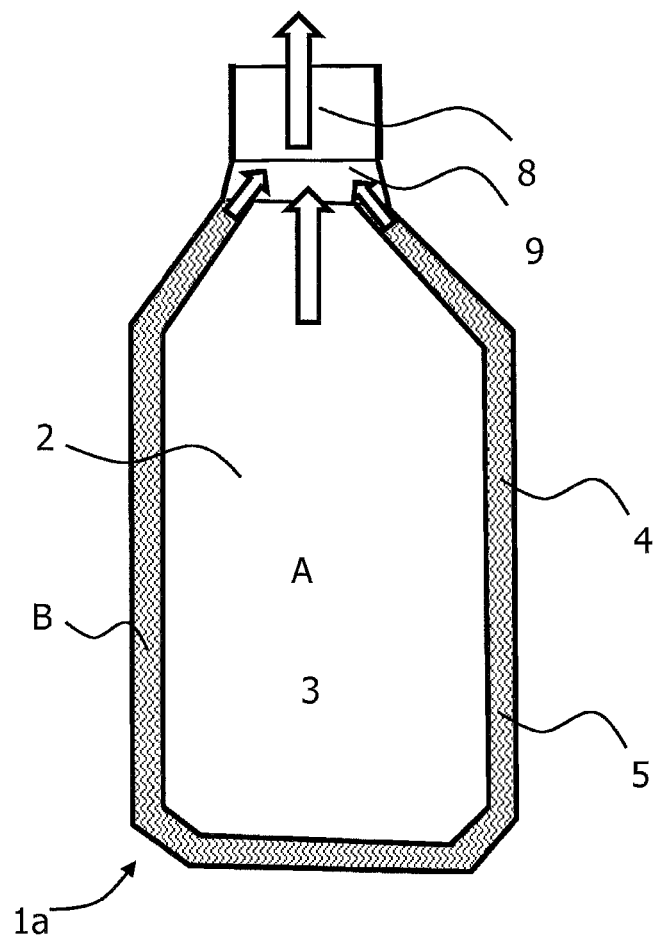
FIG. 1a illustrates a disinfectant dispenser that is configured as a double wall container.

In the embodiment of FIG. 1a the storage container 4 of the marking agent is configured in the double wall cavity B while the disinfectant is arranged in the inner cavity A. The marking agent 5 included in the double wall cavity exits from the double wall into the activation section 9 when external pressure is applied and is activated by the mixing process with the disinfectant that is performed at his location. The disinfectant that is mixed now with the activated marking agent then moves into the dispensing opening which is herein for example the opening of the double wall tube and is available for the marking disinfection.

By the same token also another non-illustrated embodiment of a stationary and also mobile disinfectant dispenser is possible where only one storage container is provided which includes already a finished mix made from the disinfectant and the marking agent. Thus the finished mix includes the marking agent in an inactive form wherein the marking agent is activated at the latest on the skin or another surface that is to be disinfected and develops its marking effect.

The marking agent can also be configured as a substance, whose molecules are configured as so called molecular switches. One example for this are spiral spiropyranes which are converted into colored merocyanin through strong ultra violet radiation and which return again into the colorless state due to a lack of UV radiation. In this case the activation section is provided as a U-V radiator.

Figure 2:
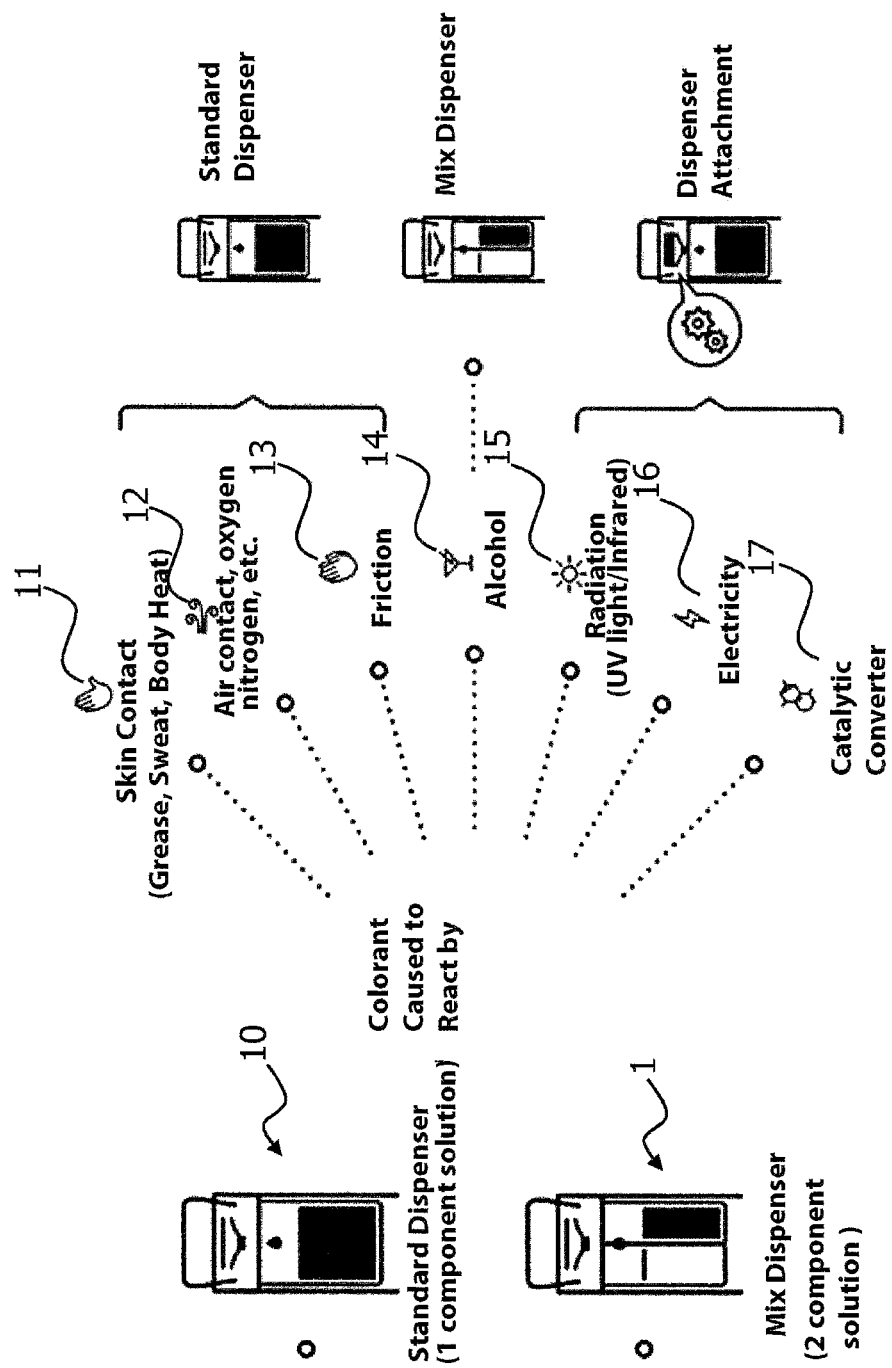
FIG. 2 illustrates a series of different and optional embodiments for disinfectant dispensers in combination with optional embodiments of the marking disinfectant.

FIG. 2 illustrates a series of different and possible embodiments for disinfectant dispensers in combination with exemplary embodiments of the marking disinfectant.

The overview illustration in FIG. 2 illustrates the disinfectant dispenser 1 on the left side that is illustrated in FIG. 1 and which is designated herein as a mixing dispenser and a disinfectant dispenser 10 that is designated as a standard dispenser where the disinfectant is already mixed with the marking agent.

In the center portion activation processes for the marking agent are illustrated. The activation of the marking agent is performed for example by a skin contact 11, an air contact 12, through friction 13 wherein this can be in particular also the inner friction for flowing liquids through a solvent 14, in particular the solvent ethanol that is widely used for disinfectants, through electromagnetic radiation 15, in particular normal day light, through electricity 16, e.g. through the piezo electric charging of a piezo crystal within the dispensing device 6 which is performed during dispensing or through an either separate catalytic converter 17 or a catalytic converter that is included in the disinfectant and which catalyzes the activation of the marking agent.

Accordingly the activations sections in the disinfectant dispenser are configured differently.

When activating the marking agent through radiation, in particular light the activation section is made in the simplest case from a window through which ambient light, in particular normal day light or the light of a room illumination can impact the marking agent arranged therein and transported through the activation section. In another variant of the activation of the marking agent through radiation the activation section includes its own light source which then radiates for example ultraviolet or infrared light onto the marking agent or the mix of the marking agent and the disinfectant.

When activating the marking agent by a catalytic converter the activation section includes a catalytic converter field through which the marking agent or the mix of the disinfectant and the marking agent is run. The catalytic converter field can for example be a coated wall which includes recesses that provide surface enlargement. In another variant the catalytic converter field includes a filling made from the catalytic converter material and includes in an ampule through which the marking agent or the mix of the marking agent and the disinfectant is run and which thus comes into an intense contact with the catalytic converter.

When activating the marking agent mechanically the marking agent is initially provided in a stabilizing microencapsulation. The activation section thus includes mechanical devices to break up the micro encapsulation wherein the marking agent is released and thus transitions into it instable and activated state. The mechanical devices can be configured in various ways in a first embodiment this is an arrangement of at least two gears that are meshing with each other or rollers that are in contact with each other. When actuating the dispensing device at the disinfectant dispenser the micro encapsulated marking agent is pressed through the gears or rollers. Thus the micro encapsulations are compressed and broken apart so that quantities of the marking agent included therein are released. The actual activation of the marking agent is then performed in its released state, for example by interaction with a solvent of the disinfectant or the surrounding air.

In one embodiment the activation section can be provided in the disinfectant dispenser wherein the inactive marking agent is compressed by high pressure or in which particles are excited to oscillate so that a first reaction is triggered which makes marking agent colored and thus provides its marking properties.

Figure 3:
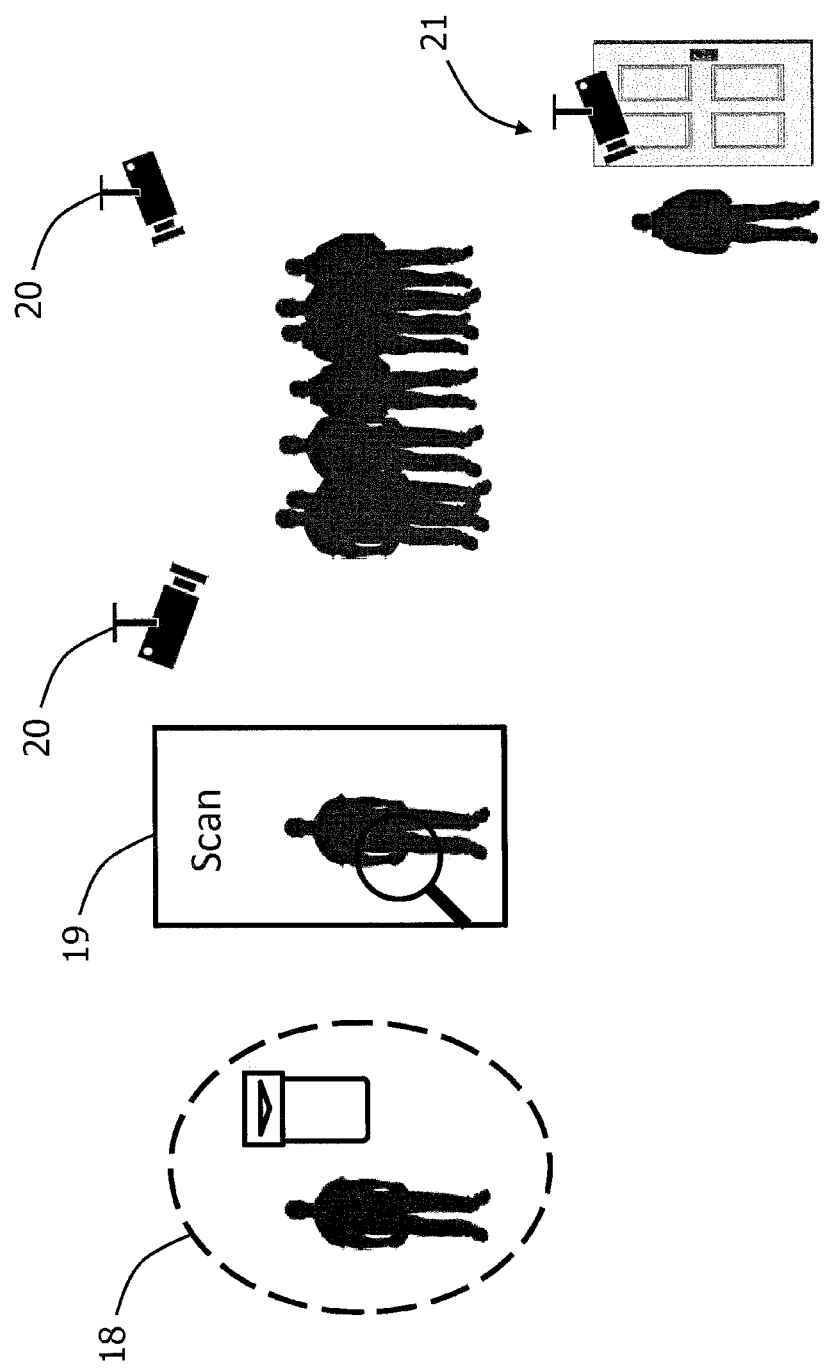
FIG. 3 illustrates an exemplary sequence of the signaling method with a series of exemplary method steps.

FIG. 3 illustrates an embodiment of the method for signaling the disinfection state of persons. The method includes plural arrangements and components which can be arranged at different locations within a defined area, for example in a hospital, a building complex or a comparable area. Furthermore an application looks promising in the care area, in particular in nursing homes, in hotels and restaurants, in industrial applications and other fields with increased requirements for cleanliness and hygiene.

It is an object of the method to cause stricter adherence to hygiene regulations. As recited supra this is achieved in that the disinfectant that is being used an additional signaling feature. The signaling feature is visible within a predetermined time period after the disinfection process at the location of the disinfection, for example on a disinfected hand. This provides a visual feedback system where the identity: "colored hands=sterile hands" is emphasized in the perception of all persons involved. Each person by themselves can determine also through the assessment of other persons when their hands or not sterile. Thus, the disinfection can hardly be omitted unintentionally. Additionally also other persons can see when the hands of persons in the area are sterile or not and can thus take corrective measures when there is a deviation. Due to these control properties behavioral optimization is induced which can lead in particular to a significant reduction of an infection rate.

The method includes at least one disinfection station 18 where the disinfection can be performed. The disinfection station thus includes in particular respectively the disinfectant dispenser 1 recited supra. The disinfectant dispenser is configured in particular according to one of the embodiments recited supra.

The disinfection stations are distributed over a corresponding area and set up at suitable locations, for example in an entry area, a reception hall, in front of access points for special stations and areas or at other suitable locations. They can be arranged in particular also in bathrooms or toilets.

When using the disinfectant dispenser an unambiguously detectable and visually perceivable marking of the disinfected body part of the person is provided in that the person rubs in the disinfectant and thus colors the skin. Typically these will be the disinfected and thus colored hands. It is thus easy to differentiate between disinfected and non-disinfected persons and to adjust one's behavior or take additional measures.

Instead of the stationary disinfection stations also portable disinfectant dispensers can be provided. These can be configured for example as tubes, portable dispensers, bottles, cans etc. and carried on a person's body. In this context a storage or a dispensing machine can be provided in an entrance area in which a particular stock of portable disinfectant dispensers is respectively provided and where entering persons can retrieve the respective individual assembles, tubes, bottles and similar articles and open them and disinfect themselves by applying the content for example to the hands.

This function is particularly relevant when coupled with image detecting systems providing access control or monitoring groups of people. The method thus includes using an access control system 19, for example provide in the form of an access gate where each person has to pass through to enter a particular area. The access control can either be provided so that the person has to hold her disinfected hands under a scanner which detects a color of the skin coloration of the scan. For example when the detection of the hand determines for example a blue skin coloration this is detected by the scanner and the person can pass the access control system. However when the hand has a typical skin color tone or another signal color the person is prevented from passing the access control system e.g. by a gate.

The access control can also be provided in a less restrictive manner. In this case image processing devices can be arranged in a typical height or hands of persons walking by are arranged. Thus a scanning process is performed while walking by thus the persons will maybe advised when passing the control arrangement to disinfect their hands and to therefore go to the next disinfection station, to retrieve a disinfection package or to disinfect themselves from the disinfection packages carried with themselves. An arrangement of this type can be arranged in particular in exits of sanitation areas wherein persons are herein requested by a respective signal to disinfect themselves.

Image capture devices of this type can also be provided at any location and can detect persons walking by and request them by acoustic, optical or voice generated signals to disinfect themselves or to refresh the disinfection.

Another aspect of the method according to the invention is monitoring and controlling larger groups of persons which are present in a particular area. For this purpose several cameras 20 are arranged in the monitored area wherein the cameras are connected with a non-illustrated central processing unit. The processing unit includes devices for image recognition and image detection, in particular a devices for registering color tones which are adapted to detect the color of the marking agent. This way an approximate statistic detection is possible how high the percentage of disinfected person is in the monitored area and how the percentage of disinfected persons is distributed location wise in a particular area. This can be the basis for initiating respective measures to improve the disinfection state in the respective areas.

Using the disinfectant works as follows:

The disinfectant is visible within a particular minimum time period. This minimum time period can be for example about one minute. An upper limit of this time period can be selected at will. The visibility of the disinfectant however should start going down at the latest as soon as the disinfecting effect subsides.

After drying the disinfectant on the hands which typically does not take more than 30 seconds the marking agent remains visible on the skin and color does not tub off. This way the control a signal effect develops. Simultaneously the disappearance of the color after a particular time period conveys that the hands of the user are most likely contaminated again after this time period. Thus it is being signaled when it is appropriate to disinfect the hands again. A process of this method can be used when there are only average requirements with respect to freedom from germs in the sense of increased cleanliness.

As another option it is provided that the skin coloration only lasts until the disinfectant has dried and all germs have been killed with a high level or probability. Thus it is also signaled to the user that his hands are actually sterile only 30 seconds after applying the disinfectant. The coloration then remains on the skin for a predetermined time period and degrades thereafter. This method is preferred when particular stringent requirements are placed upon freedom from germs. It is thus signaled to the users that a really high level of sterility of the hands is only provided for a very limited time period so that the disinfection has to be repeated.

It is advantageous when the degradation of the coloring correlates directly with a resurgent germ infestation. Thus, the degradation of the coloration can be caused directly by the starting new germ infestation, for example when contaminated objects have been touched. In this case it is advantageous that the marking agent is biodegradable wherein the marking effect degrades due to biological breakdown, for example through processing the colorant by micro biological digesting processes or through micro biological digestion products. In this case the marking agent remains visible on the skin also after drying the disinfectant. Contacting an object that is germ infested, however, has the effect that the germs provided in the marked area break down the marking agent either by assimilation in the marking agent or by releasing enzymes which destroy the molecular structure of the marking agent.

For various time based and/or spatial moments of the hand disinfection e.g. before or after entering the hospital room disinfectants that are provided with different marking agents can be used. Thus another signaling is provided which signals reliably to everybody that hands that were colored blue before entering the hospital room and hands that are colored red before leaving the hospital room are desired and required.

The coloration can also indicate a particular disinfectant type and cause a signaling of its strength and effectiveness. Particularly effective disinfectant color e.g. the disinfectant portions pink wherein it is being signaled that a particularly effective disinfectant has been used in this case where a longer dwelling time is provided. This can be supplemented with indications that particular areas, for example particular treatment rooms may only be entered when a color of this type can be provided on the disinfected skin. Thus, in particular a scanning device can be provided that is coupled with an access control system and which only allows access when the corresponding color tone has been registered. This is indicated in FIG. 3 by the reference numerals 21. Additionally this can signal that increased care has to be taken in areas where particular disinfectants with particular properties have to be used.

Instead of a temporarily visible hand disinfectant an embodiment of the disinfectant and its use can be provided that function as follows:

After entering a hospital room a hand disinfectant with a marking agent is used initially which initially colors the hands permanently. Thus it being signaled within the hospital room that hand are disinfected and cleaned from all germs that have been brought in from the outside.

Before leaving the hospital room a second hand disinfectant is being used which includes a coloring substance which deactivates the colorant that is applied from by the first disinfectant. Thus the hands are decolored again by the second disinfectant examples for this marking agent in combination with a decoloring disinfectant can be for example betanin as a colorant and sodium hypo chloride as a decoloring disinfectant.

This method makes sense e.g. when a quarantine area shall be entered. Thus, it is signaled by coloring the hands in the beginning that the first disinfection does not introduce external germs whereas it is signaled outside of the quarantine area by the hands that are decolored again due to the second disinfection that no germs are carried out of the quarantine area.

The implementation of the signaling method can be performed by removal or bleaching of colorants which are caused by the oxidizers like hydrogen peroxide or sodium hypo chloride that are provided in the disinfectants. Examples can be for example food colorants like anthocyanes (delphinidin, cyanidine) or indigo, methylene blue, betanin and brilliant blue.

As marking agents which are added to the disinfectants and which show the activatable marking properties described supra the following colorant classes are suitable.

A first colorant class is formed by photo chromic colorants. For these the marking color change is performed by light. The color change that occurs under light can be used to activate the marking agent. As soon as the marking agent has been applied to a hand and exposed to ambient light the marking coloration becomes apparent. The marking coloration can be bleached again by ambient light and can disappear. Thus, it has proven advantageous that the time period for bleaching coincides with the time period for increasing contamination after the disinfecting effect has subsided or is shorter so that the bleached color reliably indicates the lack of a disinfecting effect.

Thermo-chromic colorants which go through a color change or an activation through thermal impact can react to the skin temperature. A cooperation with the cooling of the skin surface caused by the evaporation of the disinfectant is also possible. As soon as the disinfectant applied to the skin evaporates the disinfecting effect typically occurs. This comes with a lowering of the surface temperature of the skin. This temperature change can be used to cause the color change of the marking agent and to thus indicate the disinfectant state.

Electro chromic colorants can be used as marking agents wherein the electro chromic properties of the colorant used when activating it in the disinfectant dispenser.

Solvato-chromic colorants whose color change is caused by a solvent can be advantageously used as a marking agent. Thus, it is possible in particular that the colorant is initially bleached when mixed with the disinfectant whereas it initially becomes visible again when the disinfectant evaporates on the skin and the disinfecting effect thus achieved becomes visible again. Thus coupling the solvato chromic properties with other properties is advantageous. Thus for example the solvato chromic colorant can also be ion chromic or halo chromic and can react to Ph. variations, in particular fall apart. Thus a degradation of the colorant on the disinfected skin is caused which leads to bleaching and thus makes the degradation of the disinfecting effect and a progressing new contamination visible again.

Also iono-chromic colorants which show a color change through the interaction with ions can be advantageously used. When used as a marking agent they display a first color when applied to the skin, for example blue which indicates the disinfected state for example of a hand whereas a color change to another color for example red is performed later under the impact of sweat secreted by the skin or in ions arranged therein. This is relevant in particular since the disinfecting agent is washed off again by skin sweat and thus its presence coincides closely with a re infestation of the skin with germs.

Also tribo-chromic colorants which indicate a color change through friction or piezo colorants this means colorants which indicate a color change through pressure can be used as marking agents. These are in particular microencapsulated colorants which can be activated through friction in particular in the disinfectant dispenser. However tribal chromic and piezo chromic colorants however can also indicate whether a person has only let the disinfectant run over his hand carelessly. In this case it can occur that the hand is not colored at all or only with a warning signal coloration. However intensive massaging of the disinfectant leads to a color change which carries a positive signal and is caused by the friction on the skin and the compression of the hand surface.

Additionally all colorants can be used as marking agents which do not change their color naturally but which can be broken down under certain conditions and thus lose their color. This property is also desirable for the photo colorants, thermos chromic, electro chromic, salvto-chromic, tribo-chromic and piezo-chromic colorants in order to not reverse the color change again.

The technical implementation of the marking agents can be provided by decoloring/bleaching of colorants through the oxidizers that are typical and permitted in disinfectants like e.g. hydrogen peroxide or sodium hypo chloride. Examples for these marking agents are food colorants like e.g. anthocyanes, e.g. delphinidine, cyanidine or indigo, methylene blue, betanin and diamond blue.

In order to reset the color change and the marking effect of the marking agent the following options can be used.

A first option is to use a colorant with a very low boiling point. In this case the colorant has for example a boiling point of 30° C. and evaporates due to the temperature change caused by skin contact. Thus, care has to be taken that the colorant does not dissipate too quickly so that a skin section that is still disinfected is not designated as contaminated again. On the other hand side this provides an increase in safety.

Another option is to have the colorant break down under the impact of light. Thus case has to be taken that the break down time of the colorant essentially coincides with the time period of reliable freedom from germs of the disinfected skin area. As another option a solution is possible where the colorant is mixed with a nano encapsulated solvent. The nano capsules break upon air contact and the solvent breaks down the colorant.

Also here a salvto-chromic colorant can be used which is broken down by particular solvents and bleaches. This can be in particular a colorant which breaks down when a particular skin flora with a sweat film is developed.

The subject matter of the invention was described in more detail with reference embodiments. Other variations and embodiments are within the scope of a person skilled in the art. Other embodiments can also be derived from the dependent claims.

REFERENCE NUMERALS AND DESIGNATIONS 1 disinfectant dispenser
2 first storage container
3 disinfectant
4 second storage container
5 marking agent
6 dispensing device
7 bar
8 dispensing opening
9 activation section
10 disinfectant dispenser, standard dispenser
11 activation through skin contact
12 activation through air contact
13 activation through friction
14 activation through solvent
15 activation through electromagnetic radiation
16 activation through electricity
17 activation through catalytic converter
18 disinfection station
19 access control system
20 camera
21 scanner at room access

The invention claimed is:

1. A method for public signaling of a disinfection state of persons, the method comprising the steps:
applying a disinfecting mix including a disinfecting component and a marking component to a skin area to be disinfected at a disinfection station (18) and/or from a portable disinfectant dispenser, the marking component comprising an anthocyanin colorant;
coloring the skin area to be disinfected by the marking component during the disinfection process;
persisting visually the coloration on the disinfected skin area, wherein the disinfection state of the skin area is signaled in a perceivable and detectable manner; and subsiding of the persistence of the coloration on or before subsiding sterility of the skin area, wherein a discoloration or change in color caused thereby is also signaled in a perceivable and detectable manner.

2. The method according to claim 1,
characterized in that
the disinfected and colored skin area is registered by an access control arrangement (19) wherein an access of persons is allowed or blocked as a result of a registration process by the access control arrangement.

3. The method according to claim 1,
characterized in that
the disinfected and colored skin area is registered by an image capture and image recognition arrangement (20, 21), wherein a disinfection monitoring of persons located in an area and/or of persons walking through particular pass through areas is provided as a result of the image capture and image recognition that is performed.

4. The method according to claim 1,
characterized in that
the visual persistence of the coloration on the disinfected skin area commences on or after a sterility of the skin area is caused by the disinfecting component.

5. A method for public signaling of a disinfection state of persons, the method comprising the steps:
applying a disinfecting mix including a disinfecting component and a marking component to a skin area to be disinfected at a disinfection station (18) and/or from a portable disinfectant dispenser;
coloring the skin area to be disinfected by the marking component during the disinfection process;
persisting visually the coloration on the disinfected skin area, wherein the disinfection state of the skin area is signaled in a perceivable and detectable manner; and
subsiding of the persistence of the coloration on or before subsiding sterility of the skin area, wherein a discoloration or change in color caused thereby is also signaled in a perceivable and detectable manner;
characterized in that
the visual persistence of the coloration on the disinfected skin area commences on or after a sterility of the skin area is caused by the disinfecting component;
characterized in that
the disinfecting component has a germicide effect, and
the visible persistence of the coloration on the skin area is caused by the germicide effect of the disinfecting component, wherein biological decomposition products thus generated cause a visible color reaction in the marking component.

6. The method according to claim 5,
characterized in that
the visible persistence of the coloration on the skin area is caused by the commencement of an evaporation process of the disinfecting component, wherein this causes a color reaction of the marking component.

7. The method according to claim 1, characterized in that a subsiding of the persistence of the marking component is caused by a disappearance of the coloration due to an impact of ambient air and an oxidizer, and/or by a bleaching due to an impact of ambient light and an oxidizer.

8. The method according to claim 1, characterized in that a subsiding of the persistence of the marking component is caused by an impact of a second disinfectant.

9. A method for public signaling of a disinfection state of persons, the method comprising the steps:
applying a disinfecting mix including a disinfecting component and a marking component to a skin area to be disinfected at a disinfection station (18) and/or from a portable disinfectant dispenser, the marking component comprising an anthocyanin colorant;
coloring the skin area to be disinfected by the marking component during the disinfection process;
persisting visually the coloration on the disinfected skin area, wherein the disinfection state of the skin area is signaled in a perceivable and detectable manner; and
subsiding of the persistence of the coloration on or before subsiding sterility of the skin area, wherein a discoloration or change in color caused thereby is also signaled in a perceivable and detectable manner;
characterized in that
a subsiding of the persistence of the marking component is caused by a disappearance of the coloration due to an impact of ambient air and an oxidizer, and/or by a bleaching due to an impact of ambient light and an oxidizer.

* * * * *